(12) United States Patent
Peters et al.

(10) Patent No.: US 10,973,973 B2
(45) Date of Patent: Apr. 13, 2021

(54) DEVICE AND METHOD FOR MONITORING AN EXTRACORPOREAL BLOOD TREATMENT

(71) Applicant: Fresenius Medical Care Deutschland GmbH, Bad Homburg v.d.H. (DE)

(72) Inventors: Arne Peters, Bad Homburg (DE); Christoph Wiktor, Gelnhausen (DE)

(73) Assignee: Fresenius Medical Gare Deutschland GmbH, Bad Homburg (DE)

( * ) Notice: Subject to any disclaimer, the term of this patent is extended or adjusted under 35 U.S.C. 154(b) by 274 days.

(21) Appl. No.: 16/008,579

(22) Filed: Jun. 14, 2018

(65) Prior Publication Data

US 2018/0318492 A1     Nov. 8, 2018

Related U.S. Application Data

(63) Continuation of application No. 13/519,223, filed as application No. PCT/EP2010/007948 on Dec. 27, 2010, now Pat. No. 10,022,485.

(30) Foreign Application Priority Data

Dec. 28, 2009    (DE) .................... 10 2009 060 668.8

(51) Int. Cl.
     *A61M 1/36*        (2006.01)
     *A61M 1/16*        (2006.01)

(52) U.S. Cl.
     CPC ........ *A61M 1/3663* (2013.01); *A61M 1/1603* (2014.02); *A61M 1/3656* (2014.02); *A61M 2205/18* (2013.01); *A61M 2205/3375* (2013.01)

(58) Field of Classification Search
CPC combination set(s) only.
See application file for complete search history.

(56) References Cited

U.S. PATENT DOCUMENTS

| 4,093,545 A | 6/1978 | Cullis |
| 4,334,988 A | 6/1982 | Milligan |

(Continued)

FOREIGN PATENT DOCUMENTS

| DE | 2552755 A1 | 8/1976 |
| DE | 2659377 A1 | 7/1977 |

(Continued)

OTHER PUBLICATIONS

Office Action for Japanese Patent Application No. 2015-167527, issued by the Japan Patent Office (JPO), dated Jul. 19, 2016, 3 pages.

(Continued)

*Primary Examiner* — Guy K Townsend
(74) *Attorney, Agent, or Firm* — Kilyk & Bowersox, P.L.L.C.

(57) ABSTRACT

A device and method for monitoring an access to a patient, an extracorporeal blood circuit and/or a dialyzing fluid system includes a centrifugal pump for conveying blood or dialyzing fluid instead of an occluding pump. Centrifugal pumps bring about a large change in flow rate by even a small change in pressure difference across the pump. The device includes a measuring unit for measuring the flow rate of blood or dialyzing fluid conveyed by the centrifugal pump, and a control and computing unit configured to determine an incorrect vascular access or malfunction if a change in measured flow rate Q is more than a predetermined amount. For example, a small drop in pressure in the venous blood line leads to a marked increase in the flow rate of the centrifugal pump, which is used as a basis for the detection of an incorrect vascular access.

15 Claims, 2 Drawing Sheets

(56) References Cited

U.S. PATENT DOCUMENTS

| | | | |
|---|---|---|---|
| 4,606,698 A | 8/1986 | Clausen et al. | |
| 4,739,492 A * | 4/1988 | Cochran | A61M 1/1656 210/321.71 |
| 4,838,865 A | 6/1989 | Flank et al. | |
| 4,923,598 A | 5/1990 | Schal | |
| 4,995,268 A | 2/1991 | Ash et al. | |
| 5,091,094 A * | 2/1992 | Veech | A61M 1/1656 210/321.71 |
| 5,399,157 A | 3/1995 | Goux et al. | |
| 5,685,989 A | 11/1997 | Krivitzki et al. | |
| 6,153,109 A | 11/2000 | Krivitzki | |
| 6,167,765 B1 | 1/2001 | Weitzel | |
| 6,210,591 B1 | 4/2001 | Krivitzki | |
| 6,221,040 B1 * | 4/2001 | Kleinekofort | A61M 1/16 604/4.01 |
| 6,235,199 B1 * | 5/2001 | Peterson | A61M 1/1656 137/599.01 |
| 6,514,419 B2 | 2/2003 | Kivitzki | |
| 6,575,927 B1 | 6/2003 | Weitzel et al. | |
| 6,709,414 B2 | 3/2004 | Weitzel et al. | |
| 6,926,838 B2 | 8/2005 | Krivitzki et al. | |
| 7,004,924 B1 * | 2/2006 | Brugger | A61M 1/3626 600/16 |
| 7,297,280 B2 | 11/2007 | Krivitzki et al. | |
| 7,473,371 B2 | 1/2009 | Krivitzki et al. | |
| 8,029,454 B2 * | 10/2011 | Kelly | A61M 1/16 604/5.01 |
| 8,133,194 B2 * | 3/2012 | Szamosfalvi | A61M 1/3437 604/6.07 |
| 8,211,048 B2 * | 7/2012 | Szamosfalvi | A61M 1/3437 604/5.04 |
| 8,246,826 B2 * | 8/2012 | Wilt | A61M 1/3649 210/258 |
| 8,357,298 B2 * | 1/2013 | Demers | A61M 1/3441 210/646 |
| 8,409,441 B2 * | 4/2013 | Wilt | A61M 1/1619 210/646 |
| 8,425,417 B2 * | 4/2013 | Leach | A61B 5/1495 600/365 |
| 8,647,290 B2 * | 2/2014 | Masala | A61M 1/3441 604/6.09 |
| 8,721,879 B2 * | 5/2014 | van der Merwe | A61M 1/3609 210/134 |
| 8,721,884 B2 * | 5/2014 | Wilt | A61M 1/1601 210/258 |
| 10,022,485 B2 * | 7/2018 | Peters | A61M 1/3656 604/6.09 |
| 2001/0021817 A1 * | 9/2001 | Brugger | A61M 1/3626 604/6.11 |
| 2001/0050256 A1 | 9/2001 | Brugger et al. | |
| 2003/0111423 A1 | 6/2003 | Krivitski | |
| 2003/0167030 A1 | 9/2003 | Weitzel et al. | |
| 2004/0147887 A1 * | 7/2004 | Hagstroem | A61F 5/445 604/332 |
| 2005/0044339 A1 * | 2/2005 | Sheets | G06F 9/384 711/206 |
| 2005/0051496 A1 | 3/2005 | Krivitski | |
| 2005/0131332 A1 * | 6/2005 | Kelly | A61M 1/3427 604/4.01 |
| 2005/0178732 A1 | 8/2005 | Krivitski | |
| 2007/0038191 A1 * | 2/2007 | Burbank | A61M 1/1611 604/317 |
| 2008/0015487 A1 * | 1/2008 | Szamosfalvi | A61M 1/3658 604/6.07 |
| 2008/0217245 A1 * | 9/2008 | Rambod | A61M 1/34 210/637 |
| 2009/0008331 A1 * | 1/2009 | Wilt | A61M 1/3621 210/647 |
| 2009/0221948 A1 * | 9/2009 | Szamosfalvi | A61M 1/3458 604/6.07 |
| 2010/0192686 A1 * | 8/2010 | Kamen | A61M 1/1621 73/290 R |
| 2011/0208105 A1 * | 8/2011 | Brandl | A61M 1/3675 604/5.01 |
| 2012/0150090 A1 * | 6/2012 | Szamosfalvi | A61M 1/3672 604/6.07 |
| 2012/0265116 A1 * | 10/2012 | Szamosfalvi | A61M 1/3675 604/6.07 |
| 2012/0330214 A1 * | 12/2012 | Peters | A61M 1/1603 604/6.11 |
| 2013/0020237 A1 * | 1/2013 | Wilt | A61M 1/1601 210/85 |
| 2013/0032536 A1 * | 2/2013 | Wilt | A61M 1/1621 210/646 |
| 2013/0037480 A1 * | 2/2013 | Wilt | A61M 1/1601 210/321.69 |
| 2013/0126413 A1 * | 5/2013 | van der Merwe | A61M 1/3465 210/321.6 |
| 2013/0155387 A1 * | 6/2013 | Wiktor | A61M 1/3626 356/39 |
| 2013/0204174 A1 * | 8/2013 | Olde | A61M 1/3656 604/6.11 |
| 2013/0204542 A1 * | 8/2013 | Olde | A61M 1/3659 702/35 |
| 2013/0280104 A1 * | 10/2013 | Heide | A61M 1/1086 417/53 |
| 2013/0304020 A1 * | 11/2013 | Wilt | A61M 1/3609 604/506 |
| 2014/0102970 A1 * | 4/2014 | Wilt | A61M 1/3672 210/321.69 |
| 2014/0221897 A1 * | 8/2014 | Szamosfalvi | A61M 1/3437 604/6.07 |
| 2014/0309611 A1 * | 10/2014 | Wilt | A61M 1/1694 604/500 |

FOREIGN PATENT DOCUMENTS

| | | |
|---|---|---|
| DE | 69305438 T2 | 4/1997 |
| DE | 19848235 C1 | 3/2000 |
| DE | 19809945 C2 | 2/2002 |
| DE | 69429877 T2 | 11/2002 |
| EP | 0300201 A1 | 1/1989 |
| EP | 0416808 A1 | 3/1991 |
| EP | 0943369 A1 | 9/1999 |
| GB | 1560660 A | 2/1980 |
| JP | H11-506682 A | 6/1999 |
| JP | 2006325750 A | 7/2006 |
| JP | 2008023269 A | 2/2008 |
| JP | 2009502446 A | 1/2009 |
| WO | 96/40316 | 12/1996 |
| WO | 0018451 A1 | 4/2000 |
| WO | 0053291 A1 | 9/2000 |
| WO | 2005044339 A2 | 5/2005 |
| WO | 2007019519 A2 | 2/2007 |
| WO | 2011079941 A1 | 7/2011 |

OTHER PUBLICATIONS

PCT International Search Report from PCP/EP2010/007948, dated May 19, 2011.

International Preliminary Report on Patentability from PCT/EP2010/007948, dated Jul. 10, 2012.

* cited by examiner

DEVICE AND METHOD FOR MONITORING AN EXTRACORPOREAL BLOOD TREATMENT

CROSS-REFERENCE TO RELATED APPLICATIONS

The present application is a continuation of U.S. patent application Ser. No. 13/519,223, having a filing date of Aug. 17, 2012, which is a national stage application from International Patent Application No. PCT/EP2010/007948, filed Dec. 27, 2010, that claims priority to Application No. DE 10 2009 060 668.8, filed in the Federal Republic of Germany on Dec. 28, 2009, each of which is expressly incorporated herein in its entirety by reference.

FIELD OF INVENTION

The present invention relates to a device for monitoring an access to a patient for an extracorporeal blood treatment apparatus with an extracorporeal blood circuit. Moreover, the present invention relates to a device for monitoring an extracorporeal blood circuit of an extracorporeal blood treatment apparatus. Furthermore, the present invention relates to a method for monitoring a patient access and an extracorporeal blood circuit in an extracorporeal blood treatment. The present invention also relates to an extracorporeal blood treatment apparatus with a monitoring device.

BACKGROUND OF THE INVENTION

In the field of medical technology, various extracorporeal blood treatment apparatuses comprising an extracorporeal blood circuit are known. The known extracorporeal blood treatment apparatuses include for example haemodialysis apparatuses and cell separators, which necessitate an access to the patient's vascular system. In extracorporeal blood treatment, blood is removed from the patient with an arterial puncture cannula via an arterial hose line, the blood being fed back to the patient with a venous puncture cannula via a venous hose line.

In order to convey the blood in the extracorporeal blood circuit, the extracorporeal blood treatment apparatuses generally comprise an occluding hose pump, in particular a roller pump. Occluding hose pumps are also generally provided in the dialyzing fluid system of extracorporeal blood treatment apparatuses. From other specialist medical fields, for example in heart bypass operations, other blood pumps are known for the operation of an extracorporeal blood circuit, in particular special centrifugal pumps designed for blood, which are characterised by causing relatively little damage to the blood.

Despite regular monitoring of the vascular access by hospital staff during extracorporeal blood treatment, there is in principle the risk of the venous puncture cannula slipping out of the patient's blood vessel unnoticed. Whereas slipping-out of the arterial cannula is associated with the sucking-in of air into the arterial hose line, the slipping-out of the venous cannula leads to the feared free flow of blood into the surroundings. If the slipping-out of the venous cannula is not detected immediately, therefore, there is the risk of the patient bleeding to death.

Various devices of differing design are known for the monitoring of the vascular access. The known monitoring devices generally rely on the safety devices which are present as standard in blood treatment apparatuses and which, in the event of an incorrect vascular access, trigger an immediate interruption to the blood flow in the extracorporeal blood circuit.

A monitoring device for a vascular access is described in International Patent Publication No. WO 99/29356 A1, wherein the strength of an electric current flowing through the fluid in the hose line is measured. U.S. Patent Publication No. 2004/0254513 describes a monitoring device, wherein the impedance between two electrodes disposed on the arterial and venous hose line is measured. A drawback is that the known devices require the creation of an electrical connection to the fluid flowing in the hose lines.

Monitoring systems are also known for monitoring both the arterial and the venous vascular access, said systems being based on a measurement of the pressure in the extracorporeal blood circuit. A drop-in pressure of 20 mmHG can be assumed in practice in the event of the venous puncture cannula slipping out. Since the nominal value of the measurement value resolution lies in practice in the region of 2 mmHG with a maximum total error between 15 and 20 mmHG, the detection of a venous disconnection proves to be difficult. A monitoring system with pressure monitoring is described for example in U.S. Pat. No. 6,221,040. The known pressure monitoring makes use of a special evaluation procedure.

Monitoring devices which can detect the outflow of blood at the puncture point are described in International Patent Publication No. WO 2006/008866 A1 and U.S. Patent Publication No. 2005/0038325. These devices comprise a moisture sensor.

SUMMARY OF THE PRESENT INVENTION

A problem underlying the present invention is to monitor, with particularly high reliability, a vascular access and/or an extracorporeal blood circuit and/or a dialyzing fluid system of an extracorporeal blood treatment apparatus without substantial changes to the blood treatment apparatus and without the use of separate components.

A solution to this problem takes place according to the present invention and advantageous embodiments described herein.

The device according to the present invention and the method according to the present invention are based on the use of a centrifugal pump for conveying blood in the extracorporeal blood circuit or dialyzing fluid in the dialyzing fluid system instead of an occluding pump. The centrifugal pump, which is also known by the term rotary pump, comprises a rotating pump impeller for conveying fluids. The fluid, which enters into the centrifugal pump via the suction pipe, is conveyed by the rotating pump impeller and forced to the exterior on a circuit. The kinetic energy of the fluid thereby absorbed increases the pressure inside the pump and pushes the fluid into the pressure pipe.

The present invention makes use of the special properties of the known centrifugal pumps when they are used to convey blood and/or dialyzing fluid. These centrifugal pumps are characterised in that a large change in the flow rate is brought about by even a small change in the pressure difference across the pump. When mention is made below of the flow rate, this is also understood to mean any other variable correlating with the flow rate which, as it were, increases with the increase in the flow rate.

The device according to the present invention comprises a measuring unit for measuring the flow rate of the blood conveyed by the centrifugal pump in the extracorporeal blood circuit and/or of the dialyzing fluid in the dialyzing fluid system as well as a control and computing unit, which is constituted such that, in the event of a change in the measured flow rate of more than a predetermined amount, it is concluded that there is an incorrect vascular access or a malfunction in the extracorporeal blood circuit or dialyzing fluid system. If, for example, there is a small drop in pressure in the venous blood line during the extracorporeal blood treatment, this leads to a marked increase in the flow rate of the centrifugal pump. This significant and sudden increase in the flow rate, which results from the characteristic flat delivery curve of the centrifugal pump, is used according to the present invention as a basis for the detection of an incorrect venous vascular access. With the monitoring of the flow rate of the centrifugal pump, it is possible to detect not only the slipping out of one of the two puncture cannulas from the patient's vascular system, but also nipping or kinking of the blood lines or dialyzing fluid lines and a leakage of the hose lines. The flow rate can in principle be measured at any point in the extracorporeal blood circuit or dialyzing fluid system.

It is advantageous that the device according to the present invention and the method according to the present invention do not make use of external components which require additional manipulations and unnecessarily restrict the patient's freedom of movement.

In a preferred embodiment of the present invention, the control and computing unit comprises a comparison unit for comparing the measured flow rate with a preset flow rate and a signal generation unit for generating a control signal when the difference between the measured flow rate and the preset flow rate is greater than a specific threshold value. This threshold value is dependent upon various factors. For example, the threshold value is dependent on the condition of the hose lines. Different threshold values can be preset depending on the various factors. A preferred embodiment provides for the imputting of data records on an input unit, said data records being characteristic of the various factors, for example of the hose set used. These data records are compared with stored data records to which specific threshold values are assigned, in order to be able to select the threshold value which corresponds to the inputted data record.

The monitoring device preferably comprises an alarm unit, which emits an acoustic and/or optical and/or tactile alarm when the control and computing unit generates the control signal.

The measuring unit for measuring the flow rate preferably comprise a flow sensor for the non-invasive measurement of the blood flow rate. The flow sensor is preferably an ultrasound flow sensor which works according to the known ultrasound Doppler method or propagation time difference method. Such ultrasound flow sensors are known to the person skilled in the art. Any other methods of measuring the flow rate known to the person skilled in the art can also be used, for example the evaluation of the motor data of the centrifugal pump, a magnetic induction flow measurement or an optical flow measurement with a laser. On the other hand, the measurement of the flow rate can also take place invasively for measurements of the flow rate in the dialyzing fluid system. All flow meters known to the person skilled in the art can be used for this purpose.

The flow sensor can in principle be disposed at any point in the extracorporeal blood circuit or the dialyzing fluid system, in particular on the arterial or venous blood line or the dialyzing fluid supply and discharge line. In particular, the flow sensor can be integrated into the device for arterial air bubble detection which is present as standard in blood treatment apparatuses.

The apparatus for extracorporeal blood treatment according to the present invention comprises the monitoring device according to the present invention. A preferred embodiment of the blood treatment apparatus according to the present invention makes provision such that the control unit of the blood treatment apparatus intervenes in the machine control when the control and computing unit of the monitoring device generates a control signal. The control unit is preferably constituted such that the centrifugal pump disposed in the extracorporeal blood circuit is stopped as an intervention into the machine control. Moreover, at least one shut-off element disposed in or on the venous blood line is preferably closed. Both the arterial and the venous hose clamp are preferably closed. In the event of an incorrect vascular access, for example when the venous puncture cannula has slipped out or a leakage is present in the hose system, the free flow of blood into the surroundings is thus immediately stopped.

An exemplary embodiment of the present invention is described in detail below by reference to the accompanying drawings.

BRIEF DESCRIPTION OF THE DRAWINGS

The accompanying drawings, which are incorporated in and constitute a part of this application, illustrate some of the embodiments of the present invention, and together with the description serve to explain the principles of the present invention.

DETAILED DESCRIPTION OF THE PRESENT INVENTION

The device according to the present invention for monitoring a vascular access or the extracorporeal blood circuit or dialyzing fluid system can form a separate unit or can also be a component of the extracorporeal blood treatment apparatus. If the monitoring device according to the present invention is a component of the blood treatment apparatus, the monitoring device according to the present invention can make use of specific subassemblies or components which are in any case present in the blood treatment apparatus.

An extracorporeal blood treatment apparatus A is described below, which comprises a device for monitoring the vascular access and the extracorporeal blood circuit and the dialyzing fluid system. A monitoring device solely for monitoring the vascular access or the extracorporeal blood circuit or the dialyzing fluid system can however also be provided.

Figure 1:
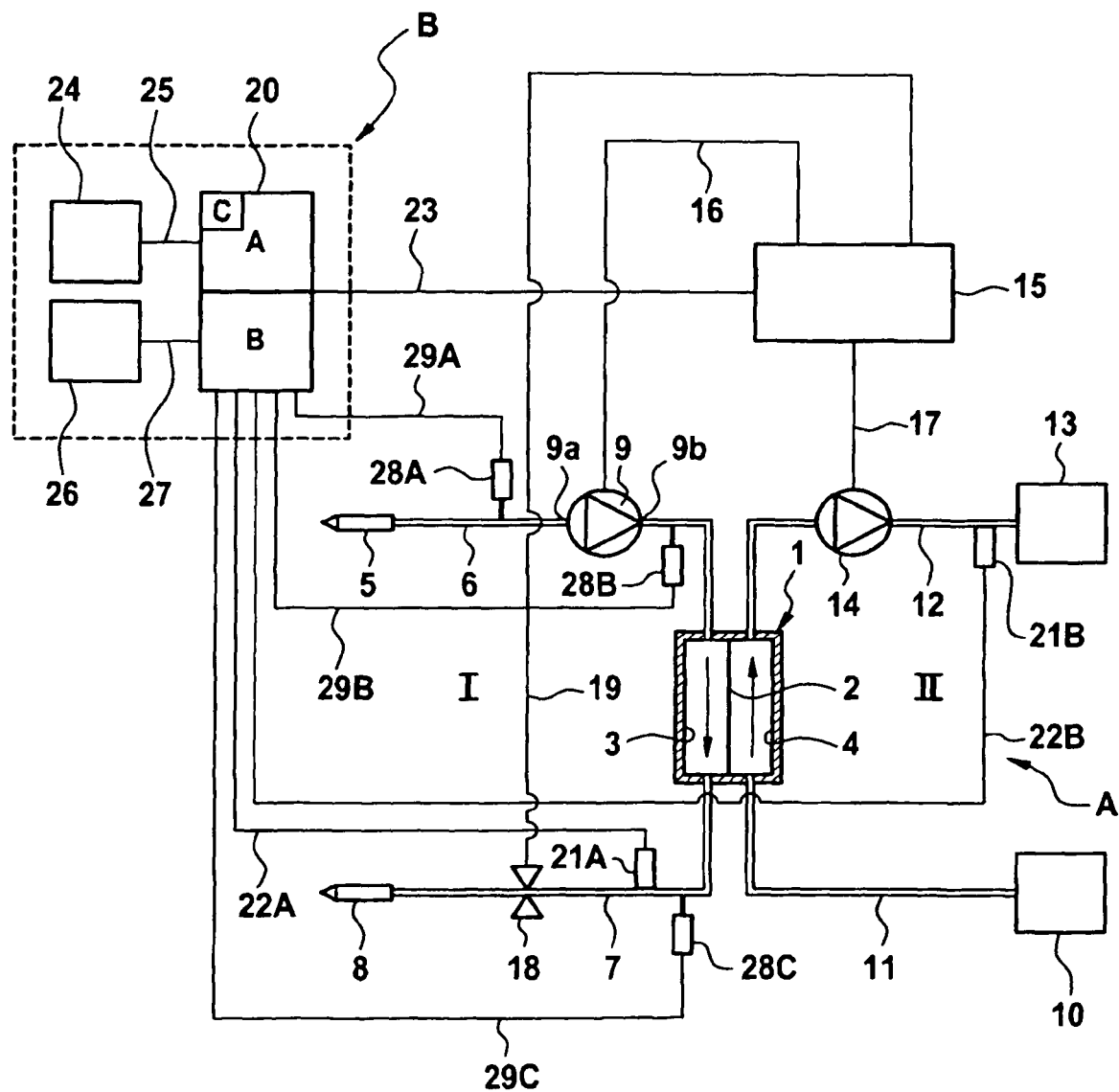
FIG. 1 shows the main components of an exemplary extracorporeal blood treatment apparatus according to the present invention, with a device according to the present invention for monitoring a vascular access or the extracorporeal blood circuit or dialyzing fluid system.

FIG. 1 shows only the main components of an exemplary blood treatment apparatus in a schematic representation, since blood treatment apparatuses as such are known to the person skilled in the art.

The blood treatment apparatus is a known haemodialysis apparatus, which comprises a dialyser 1 which is divided by a semi-permeable membrane 2 into a blood chamber 3 and a dialyzing fluid chamber 4. Connected by an arterial puncture cannula 5 to the shunt or a fistula of the patient is arterial hose line 6 which leads to the inlet of blood chamber 3 of the dialyser. Leading away from the outlet of blood chamber 3 of the dialyser is a venous hose line 7, which is connected by a venous puncture cannula 8 to the shunt or the fistula. The blood is conveyed in extracorporeal blood circuit I by a centrifugal pump 9, which is provided on arterial hose line 6. The centrifugal pump is a pump specially designed for blood, which is characterised by causing little damage to the blood.

Dialyzing fluid system II of the haemodialysis apparatus comprises a dialyzing fluid source 10, to which a dialyzing fluid supply line 11 is connected, which leads to the inlet of dialyzing fluid chamber 4 of the dialyser. Leading away from the outlet of dialyzing fluid chamber 4 of the dialyzer is a dialyzing fluid discharge line 12 which leads to an outlet 13. The dialyzing fluid is conveyed in the dialyzing fluid circuit by a dialyzing fluid pump 14, which is disposed on dialyzing fluid discharge line 12. In the present example embodiment, the monitoring device is also used to monitor the dialyzing fluid system. Dialyzing fluid pump 14 is therefore also a centrifugal pump. This is not necessary, however, if the monitoring device is used solely to monitor the vascular access or the extracorporeal blood circuit.

The control of the dialysis apparatus is assumed by a central control unit 15, which controls blood pump and dialyzing-fluid pump 9, 14 via control lines 16, 17. Located downstream of blood chamber 3 of the dialyser on venous hose line 7 is an electromagnetically operated hose clamp 18, which can be opened or closed by central control unit 15 via a further control line 19. When venous hose clamp 18 is closed, the fluid flow in extracorporeal blood circuit I is interrupted, so that blood cannot pass into the surroundings.

Monitoring device B comprises a control and computing unit 20, which is represented in FIG. 1 as a separate unit. Control and computing unit 20 can however also be a component of central control unit 15 of the blood treatment apparatus.

Moreover, monitoring device B comprises a measuring unit for measuring the flow rate of the blood conveyed in extracorporeal blood circuit I by centrifugal pump 9 and a measuring unit for measuring the flow rate of the dialyzing fluid conveyed in a dialyzing fluid system II by centrifugal pump 14. The measuring unit for measuring the flow rate in extracorporeal blood circuit I comprises a flow sensor 21A, which in the present example embodiment is disposed downstream of dialyzing fluid chamber 3 of dialyser 1 and upstream of hose clamp 18 on venous blood line 7, whilst the measuring unit for measuring the flow rate of the conveyed dialyzing fluid comprises a flow sensor 21B, which is disposed downstream of dialyzing fluid pump 14. In the present example embodiment, flow sensors 21A and 21B are ultrasound flow sensors for the non-invasive measurement of the flow rate of the blood and the dialyzing fluid respectively. The measured values of ultrasound flow sensors 21A and 21B are received by control and computing unit 20 via data lines 22A and 22B.

Control and computing unit 20 comprises a comparison unit 20A for comparing the measured flow rate with a preset flow rate. Moreover, control and computing unit 20 comprises a signal generation unit 20B for generating a control signal which is received by central control unit 15 via a data line 23.

A specific blood flow rate is set for the extracorporeal blood treatment by the doctor in charge. Central control unit 15 of the blood treatment apparatus sets speed n of centrifugal pump 9 such that the blood in extracorporeal blood circuit I is conveyed at a preset flow rate. The preset flow rate is measured by flow sensor 21A. This flow rate corresponds to the flow rate of centrifugal pump 9, which is preset as a reference value in control and computing unit 20. This flow rate is therefore referred to as the preset flow rate. The flow rate of the blood is now continuously monitored during the extracorporeal blood treatment. The flow rate measured by flow sensor 21A is constantly compared with the flow rate previously preset as a reference value. The difference between the measured flow rate and the preset flow rate is worked out. If the difference is greater than a specific threshold value, control and computing unit 20 generates a control signal, which is received by central control unit 15 via data line 23.

Figure 2:
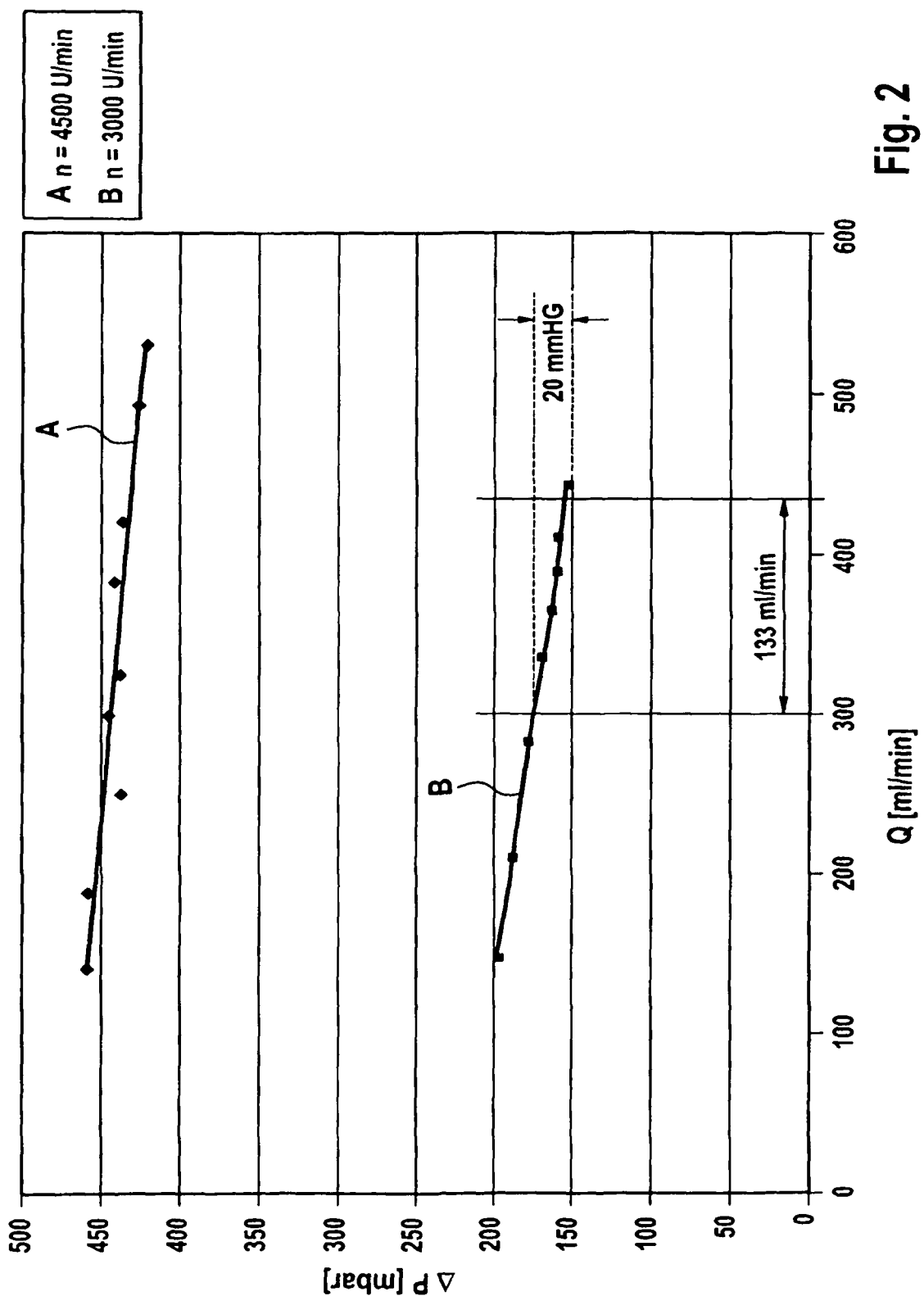
FIG. 2 shows the basic course of the pressure difference across the exemplary centrifugal pump present in the extracorporeal blood circuit as a function of the blood flow.

FIG. 2 shows the pressure difference between inlet 9a and outlet 9b of an exemplary centrifugal pump 9 as a function of flow rate Q. The slipping-out of venous puncture cannula 8 leads to a change in pressure ΔP of 20 mmHG across centrifugal pump 9 in extracorporeal blood circuit I. FIG. 2 shows that, with a speed n of 3000 revs/min, blood flow rate Q of 300 ml/min increases by 133 ml/min. At 4500 revs/min, a volume flow increase of 235 ml/min can be seen. The two characteristic curves (characteristic curve A 4500 revs/min and characteristic curve B 3000 revs/min) show that even a small change in pressure ΔP of 20 mmHG leads to a significant increase in flow rate Q.

Control and computing unit 20 compares the difference between the measured flow rate and the preset flow rate with a specific threshold value. If the difference is greater than the threshold value, i.e. a significant increase in the flow rate is recorded, an incorrect vascular access is assumed, and the control signal is generated.

Monitoring device B comprises an alarm unit 24, which receives the control signal of control and computing unit 20 via a data line 25. Alarm unit 24 then emits an acoustic and/or optical and/or tactile alarm. The alarm unit can however also be a component of the blood treatment apparatus. When central control unit 15 of the blood treatment apparatus receives the control signal of control and computing unit 20, central control unit 15 stops centrifugal pump 9 immediately and immediately closes hose clamp 18, so that the free flow of blood into the surroundings is immediately stopped.

Monitoring device B also comprises an input unit 26, which is connected via a data line 27 to control and computing unit 20. Input unit 26 can also be a component of the blood treatment apparatus.

Various parameters can be inputted on input unit 26 of monitoring device B, said parameters including for example the data describing employed hose system 6, 7, which indicate for example the internal diameter, the wall thickness or the material of the hose lines. The data input can take place manually or automatically, for example by means of a barcode, matrix code, RFID etc. Control and computing unit 20 comprises a memory 20C, in which specific threshold values for the monitoring of the vascular access are assigned to various data records. Control and computing unit 20 compares the data records inputted on input unit 26 with the assigned data records and selects the threshold value that corresponds to the inputted data record. This ensures that different threshold values for the monitoring of the vascular access can be made available for different hose lines.

The threshold value can in principle also be dynamically variable. On the one hand, the threshold value can be preselected as fixed by the user, for example before the start of the treatment. On the other hand, the threshold value can also be adapted during the treatment. The adaptation can also take place automatically. For example, slow changes in the flow can occur due to viscosity changes in the blood or also a change in the filter properties. In order not to trigger an alarm in such cases, the threshold value can be automatically adapted accordingly. The alarm limits for abrupt changes in the flow rate can also be "carried along" until a preset limit is reached. "Preset" is understood in this connection to mean that the threshold value is present or made available in the evaluation unit before its use.

The monitoring of the flow rate of the dialyzing fluid in order to detect a malfunction in dialyzing fluid system II takes place in a similar manner to the monitoring of the blood flow rate, wherein the dialyzing fluid rate measured by flow sensor 21B is compared with a preset flow rate. If the difference between the measured and preset flow rate is greater than a specific threshold value, it is concluded that there is a malfunction in the dialyzing fluid system. This malfunction may again lie in a kinked or nipped hose line or a leakage.

In a preferred embodiment, the rate of change of the flow rates in the hose lines is monitored, wherein the hose lines may be arterial and venous blood line 6, 7 or dialyzing fluid supply or discharge line 11, 12. The rate of change of the flow rate is compared with a preset threshold value. It is concluded that there is a malfunction especially in the case of a sudden change in the flow rate. In addition to the monitoring of the flow rates, the pressure characteristics in the hose lines can also be monitored. It is thus possible to distinguish between specific malfunctions, for example between a disconnection of a cannula or a leakage or the clogging up of dialyser 1. In a preferred embodiment, pressure sensors for measuring the pressure in the hose lines are provided for this purpose.

FIG. 1 shows a pressure sensor 28A for measuring the pressure in arterial blood line 6 upstream of blood pump 9 and a pressure sensor 28B for measuring the pressure in arterial blood line 6 downstream of blood pump 9 as well as a pressure sensor 28C for measuring the pressure in venous blood line 7. Pressure sensor 28A is connected via a data line 29A, pressure sensor 28B is connected via a data line 29B and pressure sensor 28C is connected via a data line 29C to control and computing unit 20.

In the preferred embodiment, control and computing unit 20 is constituted such that a distinction can be made between the cases stated below.

If the blood flow rate in extracorporeal blood circuit I measured by flow sensor 21A falls at a rate which is greater than a preset first threshold value, and the pressure measured by pressure sensor 28A upstream of blood pump 9 falls below a preset threshold value, control and computing unit 20 concludes that the blood line is kinked or nipped.

If the blood flow rate in extracorporeal blood circuit I measured by flow sensor 21A falls at a rate which is greater than a preset second threshold value, and the pressure measured by pressure sensor 28B downstream of blood pump 9 increases above a preset threshold value, control and computing unit 20 concludes that the blood line is kinked or nipped.

If the blood flow rate in extracorporeal blood circuit I measured by flow sensor 21A falls at a rate which is greater than a preset third threshold value which is less than the aforementioned first threshold value, i.e. the flow rate falls more slowly, and the pressure measured by pressure sensor 28B downstream of blood pump 9 increases above a preset threshold value, control and computing unit 20 concludes that dialyser 1 is clogged up.

If the blood flow rate in extracorporeal blood circuit I measured by flow sensor 21A increases at a rate which is greater than a preset fourth threshold value, i.e. the flow rate increases rapidly, and the pressure measured by pressure sensor 28C in venous blood line 7 remains constant or falls, control and computing unit 20 concludes that a disconnection of venous cannula 8 is present.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A device for monitoring an extracorporeal blood treatment apparatus that comprises an extracorporeal blood circuit and a dialyzing fluid system, the extracorporeal blood circuit having an arterial blood line with an arterial patient connection and a venous blood line with a venous patient connection, wherein a centrifugal pump for conveying blood in the extracorporeal blood circuit is disposed in one of the arterial blood line or the venous blood line, the device comprising:
   a flow sensor configured to measure flow rate Q of the blood conveyed by the centrifugal pump in the extracorporeal blood circuit; and
   a control and computing unit configured to
      compare a rate of change of a measured flow rate Q with a specific threshold value,
      determine that at least one of an incorrect vascular access and a malfunction in the extracorporeal blood circuit is present when the rate of change of the measured flow rate Q is more than the specific threshold value, and
      generate a control signal to activate an alarm unit, stop the centrifugal pump, or both, when the control and computing unit determines that at least one of an incorrect vascular access and a malfunction in the extracorporeal blood circuit is present.

2. A device for monitoring an extracorporeal blood treatment apparatus that comprises an extracorporeal blood circuit and a dialyzing fluid system, the dialyzing fluid system having a dialyzing fluid supply line and a dialyzing fluid discharge line, wherein a centrifugal pump for conveying dialyzing fluid is disposed in one of the dialyzing fluid supply line or the dialyzing fluid discharge line, the device comprising:
   a flow sensor configured to measure flow rate Q of the dialyzing fluid conveyed by the centrifugal pump in the dialyzing fluid system; and a control and computing unit configured to compare a rate of change of a measured flow rate Q with a specific threshold value, determine that a malfunction in the dialyzing fluid system is present when the rate of change of the measured flow rate Q is more than the specific threshold value, and generate a control signal to activate an alarm unit, stop the centrifugal pump, or both, when the control and computing unit determines that a malfunction in the dialyzing fluid system is present.

3. A method for monitoring an extracorporeal blood treatment apparatus that comprises an extracorporeal blood circuit and a dialyzing fluid system, the extracorporeal blood circuit having an arterial blood line with an arterial patient connection and a venous blood line with a venous patient connection, wherein a centrifugal pump for conveying blood in the extracorporeal blood circuit is disposed in one of the arterial blood line or the venous blood line, the method comprising:

measuring flow rate Q of the blood conveyed by the centrifugal pump in the extracorporeal blood circuit;

comparing a rate of change of a measured flow rate Q with a specific threshold value;

determining that at least one of an incorrect vascular access and a malfunction in the extracorporeal blood circuit is present when the rate of change of the measured flow rate Q is more than the specific threshold value; and generating a control signal to activate an alarm unit, stop the centrifugal pump, or both, after the step of determining that at least one of an incorrect vascular access and a malfunction in the extracorporeal blood circuit is present.

4. A method for monitoring an extracorporeal blood treatment apparatus that comprises an extracorporeal blood circuit and a fluid dialyzing system, the extracorporeal blood circuit having an arterial blood line with an arterial patient connection and a venous blood line with a venous patient connection, the dialyzing fluid system having a dialyzing fluid supply line and a dialyzing fluid discharge line, wherein a centrifugal pump for conveying dialyzing fluid is disposed in one of the dialyzing fluid supply line or the dialyzing fluid discharge line, the method comprising:

measuring flow rate Q of the dialyzing fluid conveyed by the centrifugal pump in the dialyzing fluid system;

comparing a rate of change of a measured flow rate Q with a specific threshold value;

determining that a malfunction in the dialyzing fluid system is present when the rate of change of the measured flow rate Q is more than the specific threshold value; and generating a control signal to activate an alarm unit, stop the centrifugal pump, or both, after the step of determining that a malfunction in the dialyzing fluid system is present.

5. The device according to claim 1, wherein the control and computing unit comprises:

a comparison unit configured to compare the rate of change of the measured flow rate Q with the specific threshold value; and a signal generation unit configured to generate the control signal when the rate of change of the measured flow rate Q is greater than the specific threshold value.

6. The device according to claim 2, wherein the control and computing unit comprises:

a comparison unit configured to compare the rate of change of the measured flow rate Q with the specific threshold value; and a signal generation unit configured to generate the control signal when the rate of change of the measured flow rate Q is greater than the specific threshold value.

7. An apparatus for extracorporeal blood treatment with an extracorporeal blood circuit, the apparatus comprising:

an arterial blood line with an arterial patient connection and a venous blood line with a venous patient connection;

a centrifugal pump configured to convey blood in the extracorporeal blood circuit and being disposed in one of the arterial blood line or the venous blood line; and the device for monitoring according to claim 1.

8. An apparatus for extracorporeal blood treatment with an extracorporeal blood circuit and a dialyzing fluid system, the apparatus comprising:

a dialyzing fluid system comprising a dialyzing fluid supply line and a dialyzing fluid discharge line;

a centrifugal pump configured to convey dialyzing fluid and being disposed in one of the dialyzing fluid supply line or the dialyzing fluid discharge line; and the device for monitoring according to claim 2.

9. The apparatus according to claim 7, further comprising a central control unit configured to receive the control signal from the control and computing unit and to activate the alarm, stop the centrifugal pump, or both.

10. The apparatus according to claim 9, further comprising a shut-off element disposed in or on the venous blood line, wherein the central control unit of the apparatus is further configured to close the shut-off element disposed in or on the venous blood line when the central control unit receives the control signal.

11. The apparatus according to claim 7, wherein the centrifugal pump is disposed in the arterial blood line.

12. The device according to claim 1, wherein the control and computing unit is further configured to monitor the rate of change of the measured flow rate Q.

13. The device according to claim 2, wherein the control and computing unit is further configured to monitor the rate of change of the measured flow rate Q.

14. The method of claim 3, further comprising determining and monitoring a rate of change of the measured flow rate Q.

15. The method of claim 4, further comprising determining and monitoring a rate of change of the measured flow rate Q.

* * * * *